(12) United States Patent
Cheong et al.

(10) Patent No.: US 7,968,331 B2
(45) Date of Patent: Jun. 28, 2011

(54) CELL CO-CULTURE APPARATUS FOR RESEARCHING CELL INTERACTION AND METHOD THEREOF

(75) Inventors: Kwang Ho Cheong, Yongin-si (KR); Chin-sung Park, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1191 days.

(21) Appl. No.: 11/626,523

(22) Filed: Jan. 24, 2007

(65) Prior Publication Data

US 2007/0249041 A1    Oct. 25, 2007

(30) Foreign Application Priority Data

Apr. 21, 2006 (KR) .......................... 10-2006-0036404

(51) Int. Cl.
*C12M 1/14* (2006.01)
*C12M 3/04* (2006.01)

(52) U.S. Cl. ............... 435/299.1; 435/294.1; 435/288.3; 435/288.4; 435/288.5; 435/305.2

(58) Field of Classification Search ............... 435/299.1, 435/288.5, 305.2
See application file for complete search history.

(56) References Cited

U.S. PATENT DOCUMENTS

| | | | |
|---|---|---|---|
| 5,635,390 A | 6/1997 | Peindl et al. | |
| 2002/0173033 A1* | 11/2002 | Hammerick et al. | 435/305.2 |
| 2004/0053403 A1* | 3/2004 | Jedrzejewski et al. | 435/287.2 |
| 2004/0214313 A1 | 10/2004 | Zhang et al. | |
| 2005/0208471 A1 | 9/2005 | Elias | |

FOREIGN PATENT DOCUMENTS

WO    2005123950    12/2005

OTHER PUBLICATIONS

A.M.P. Turner, et al. "Attachment of astroglial cells to microfabricated pillar arrays of different geometries", Pub Jun. 28, 2000, Journal of Biomedical Materials Research Part A, vol. 51, Issue 3, pp. 430-441.*
Endothelial Cells Stimulate Self-Renewal and Expand Neurogenesis of Neural Stem Cells; Quin Shen, Susan K. Goderie, Li Jin, Nithin Karanth, Yu Sun, Natalia Abramova, Peter Vincent, Kevin Pumiglia, Sally Temple; May 28, 2004, vol. 304; SCIENCE; pp. 1338-1340.
European Search Report; EP06127331; Aug. 1, 2007 All references cited in the Search Report and not previously submitted are listed above.

* cited by examiner

*Primary Examiner* — William H Beisner
*Assistant Examiner* — Danielle Henkel
(74) *Attorney, Agent, or Firm* — Cantor Colburn LLP

(57) ABSTRACT

A cell co-culture apparatus and a method of co-culturing and isolating cells using the cell co-culture apparatus to research interactions between cells by direct contact between the cells are provided. The cell co-culture apparatus includes a first substrate including a substrate portion and a plurality of projections provided on a surface of the substrate portion, each of the projections having a top surface for culturing cells, a second substrate including a same number of first channels as a number of the projections such that the channels fit with the projections and substrate surfaces formed between the first channels, and a third substrate including a plurality of second channels corresponding with the top surfaces and a plurality of third channels corresponding with the substrate surfaces.

18 Claims, 12 Drawing Sheets

FIG. 12
A
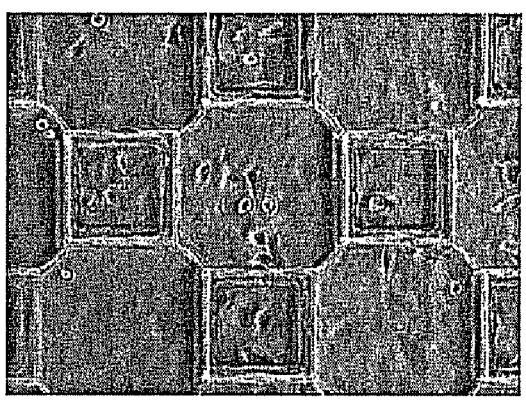
B
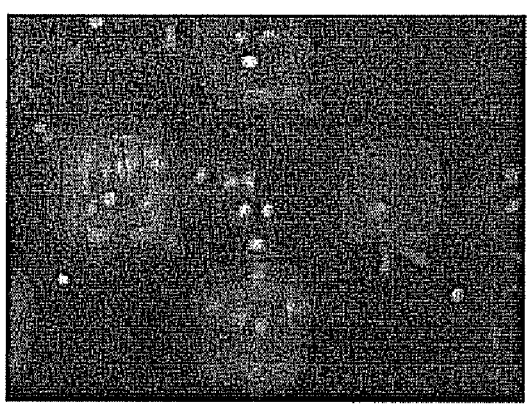
C
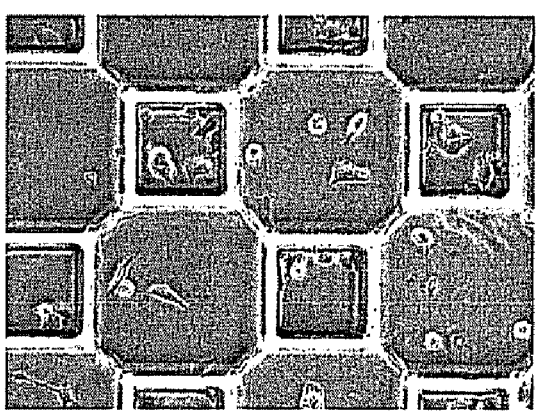
D
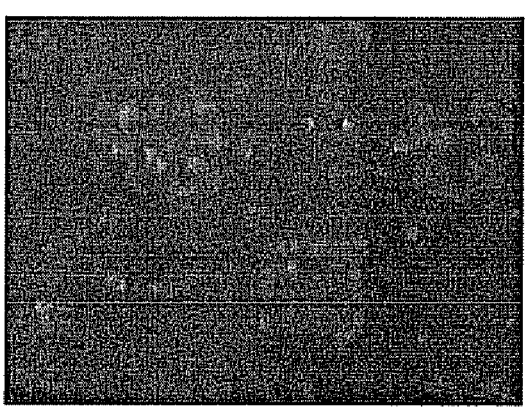

FIG. 13
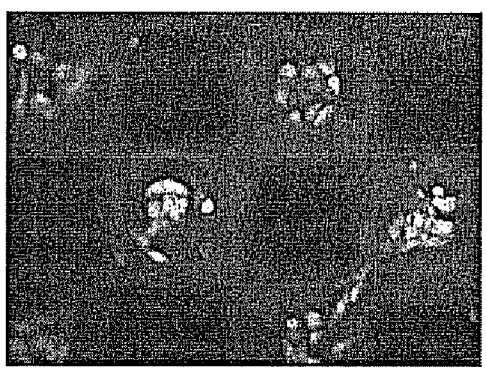
A
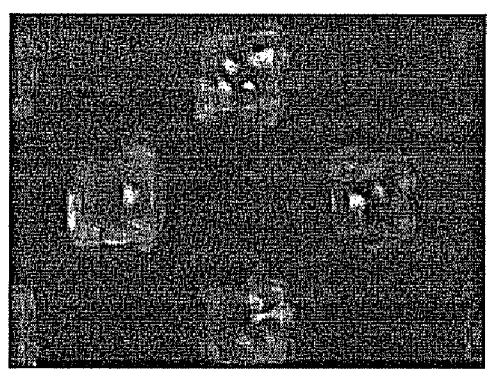
B
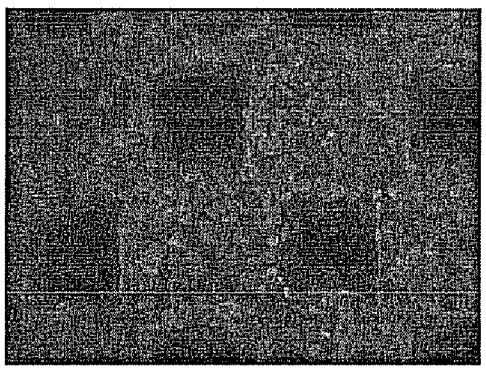
C
D

CELL CO-CULTURE APPARATUS FOR RESEARCHING CELL INTERACTION AND METHOD THEREOF

This application claims priority to Korean Patent Application No. 10-2006-0036404, filed on Apr. 21, 2006, and all the benefits accruing therefrom under 35 U.S.C. §119, the contents of which are incorporated herein in its entirety by reference.

BACKGROUND OF THE INVENTION

1. Field of the Invention

The present invention relates to a cell co-culture apparatus for researching interactions between cells. More particularly, the present invention relates to a cell co-culture apparatus for researching interactions between cells by direct contact between cells.

2. Description of the Related Art

Interactions between cells are very important in growth, migration, and differentiation of cells. Furthermore, tissues serve their functions by interactions between cells, and thus, in in vitro cell research, interactions between cells are significantly important. Thus, a means that allows the research on interactions between cells by direct contact is required.

At a specific molecular level, the interactions between the cells include signal transfers between the cells through body fluids, such as growth hormones and cytokines, etc., and signal transfers by direct contact between the cells.

Representative examples of signal transfers by direct contact between cells include interactions between a hematopoietic stem cell ("HSC") and spindle-shaped N-cadherin osteoblast ("SNO"). As illustrated in FIG. 1B, the HSC interacts with the SNO via N-cadherin to retain stemness. That is, in order to retain the stemness of the HSC, the SNO must be adjacent to the HSC, as schematically illustrated in FIG. 1A.

In Shen Q. et al., endothelial cells provide circumstances wherein the stemness of neural stem cells are retained using a transwell insert. (Shen Q et al., Endothelial cells stimulate self-renewal and expand neurogenesis of neural stem cells. Science. 2004 May 28; 304 (5675):1338-40). In Shen Q. et al., the research on the interactions between the endothelial cells and the neural stem cells was performed using the transwell insert. Specifically, the transwell insert is used as illustrated in FIG. 2.

Referring to FIG. 2, two types of cells that are to be investigated for their interaction with each other are separated from each other by the transwell insert. Thus, in the above-mentioned research, only the interactions between the cells by soluble factors may be researched through liquids. An apparatus for researching the interactions by direct contact between the cells has not been provided and thus is required.

BRIEF SUMMARY OF THE INVENTION

Exemplary embodiments of the present invention provide a cell co-culture apparatus for researching interactions between cells.

Exemplary embodiments of the present invention provide a method of co-culturing and isolating cells using the above cell co-culture apparatus.

An exemplary embodiment of a cell co-culture apparatus is designed for culturing at least two different types of cells that are in contact with each other at the interface between the two different types of cells and isolating one of the different types of cells from the other in order to confirm a change in each of the cells during the contact culture. The cell co-culture apparatus is a set including three substrates. The first substrate is for seeding and culturing the first cells among the cells that are to be investigated for the cell interaction, the second substrate is for seeding and culturing the second cells from among the cells that are to be investigated for the cell interaction, and the third substrate is for providing channels through which the first cells and the second cells may relatively easily be seeded in the first substrate and the second substrate.

In an exemplary embodiment there is provided a cell co-culture apparatus including a first substrate having a substrate portion and a plurality of projections on a surface of the substrate portion, the projections having top surfaces for culturing cells, a second substrate having a same number of first channels as a number of the projections of the first substrate such that the first channels fit with the projections of the first substrate and substrate surfaces interposed between the first channels, and a third substrate having a plurality of second channels corresponding with the top surfaces of the projections of the first substrate and a plurality of third channels corresponding with the substrate surfaces of the second substrate.

In an exemplary embodiment, the first substrate may further include at least one fixing pillar and the second substrate and the third substrate each may further includes at least one fixing channel into which the at least one fixing pillar is inserted.

In an exemplary embodiment, a thickness of the second substrate may be the same as a height of the projections of the first substrate. Alternatively, the thickness of the second substrate may be different from the height of the projections of the first substrate, provided that after cells are seeded in the first substrate and a different type of cells are seeded in the second substrate, the interaction between the different types of cells can be observed during the co-culture of the cells.

In an exemplary embodiment, the substrate portion of the first substrate includes glass, silicon, plastics, or a combination thereof, but is not limited thereto.

In an exemplary embodiment, the projections of the first substrate, the second substrate, and the third substrate each may be formed of a biocompatible material, preferably SU-8.

In an exemplary embodiment, a width, a length and a height of the projections of the first substrate may each be about 50 μm to about 100 μm. A width and a length of the first channels of the second substrate and a thickness of the second substrate may each be about 50 μm to about 100 μm. A width and a length of the second and third channels of the third substrate and a thickness of the third substrate may each be about 50 μm to about 100 μm.

In an exemplary embodiment, there is provided a method of co-culturing and isolating cells using the cell co-culture apparatus. The method includes disposing a second substrate on a first substrate such that a plurality of first channels of the second substrate fit with a plurality of projections of the first substrate, respectively, disposing a third substrate on the second substrate such that a plurality of second channels of the third substrate correspond with top surfaces of the projections of the first substrate and substrate surfaces between the channels of the second substrate, respectively, seeding first cells on the top surfaces of the projections of the first substrate and second cells on the substrate surfaces between the first channels of the second substrate through the second channels of the third substrate, separating the third substrate from the second substrate and culturing the cells, and separating the second substrate from the first substrate.

In an exemplary embodiment, the same or different type of the first cells may be seeded on each of the top surfaces of the projections of the first substrate. Also, the same or different type of the second cells may be seeded on each of the substrate surfaces between the channels of the second substrate.

In an exemplary embodiment, there is provided a method of co-culturing and isolating cells using the cell co-culture apparatus. The method includes disposing a second substrate on a first substrate such that a plurality of first channels of the second substrate fit with a plurality of projections of the first substrate for each of a first set of the substrates and a second set of the substrates, respectively, a first co-culture apparatus including the first set of the substrates and a second co-culture apparatus including the second set of the substrates, disposing a third substrate on the second substrate such that a plurality of second channels of the third substrate correspond with top surfaces of the projections of the first substrate and substrate surfaces between the first channels of the second substrate, respectively, for each of the first set of the substrates and the second set of the substrates, seeding first cells through all of the second channels of the third substrate in the first cell co-culture apparatus, seeding second cells through all of the channels of the second channels third substrate in the second cell co-culture apparatus, and separating the first substrate, the second substrate, and the third substrate from each other, respectively, for each of the first and second cell co-culture apparatuses, disposing the second substrate of the second cell co-culture apparatus on the first substrate of the first cell co-culture apparatus and disposing the second substrate of the first cell co-culture apparatus on the first substrate of the second cell co-culture apparatus such that the first channels of the second substrates of each of the first and second cell co-culture apparatus fit with the projections of each of the first substrates, respectively, and culturing the first and the second cells, and separating the second substrates of each of the first and second cell co-culture apparatus, respectively, from the first substrates of each of the first and second cell co-culture apparatus, respectively.

BRIEF DESCRIPTION OF THE DRAWINGS

The above and other features and advantages of the present invention will become more apparent by describing in detail exemplary embodiments thereof with reference to the attached drawings in which.

FIG. 12 is microscopic photographs of an exemplary embodiment of cells inoculated in a cell co-culture apparatus according to the present invention, the photographs being taken after a third substrate is separated from the apparatus; and FIG. 13 is microscopic photographs of an exemplary embodiment of cells on a first substrate and a second substrate co-cultured in a cell co-culture apparatus according to the present invention, the photographs being taken after the first and second substrates are separated from the apparatus.

DETAILED DESCRIPTION OF THE INVENTION

Figure 1A:
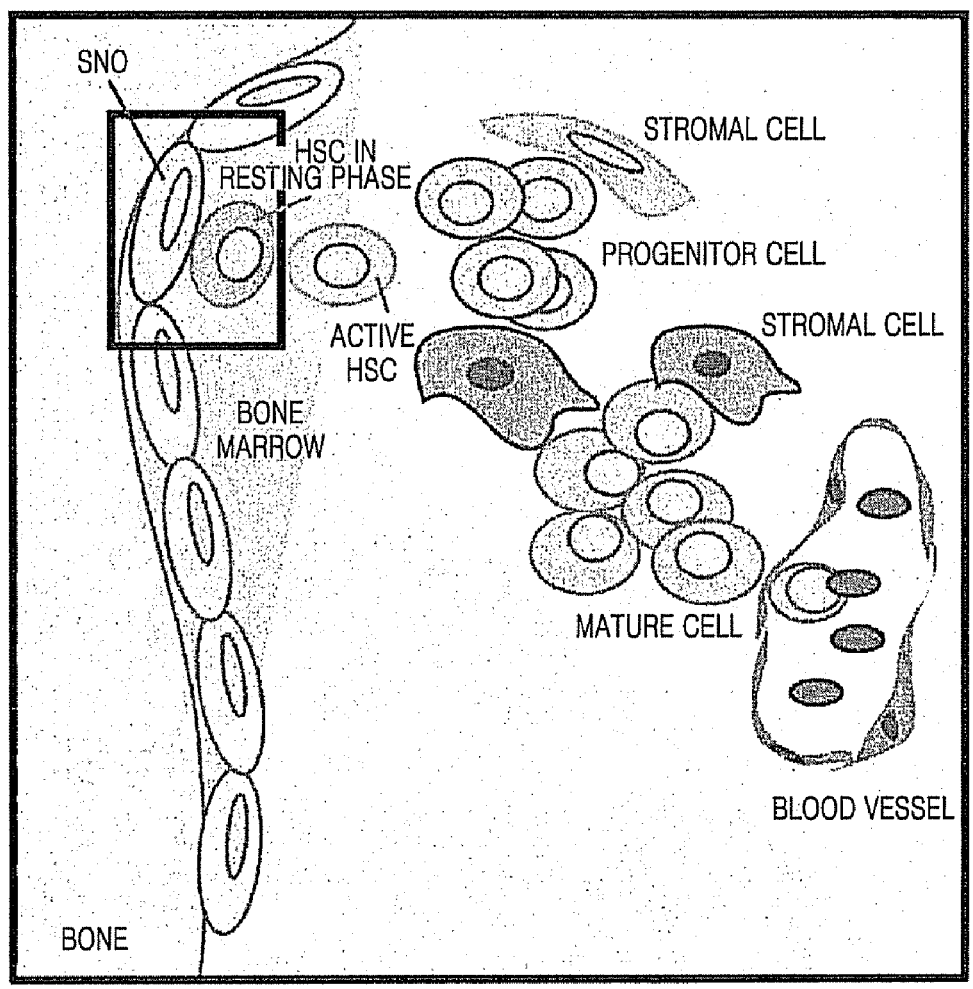
FIG. 1A is a schematic view illustrating a hematopoietic stem cell ("HSC") in a resting phase adjacent to spindle-shaped N-cadherin osteoblast ("SNO") in humans.
Figure 1B:
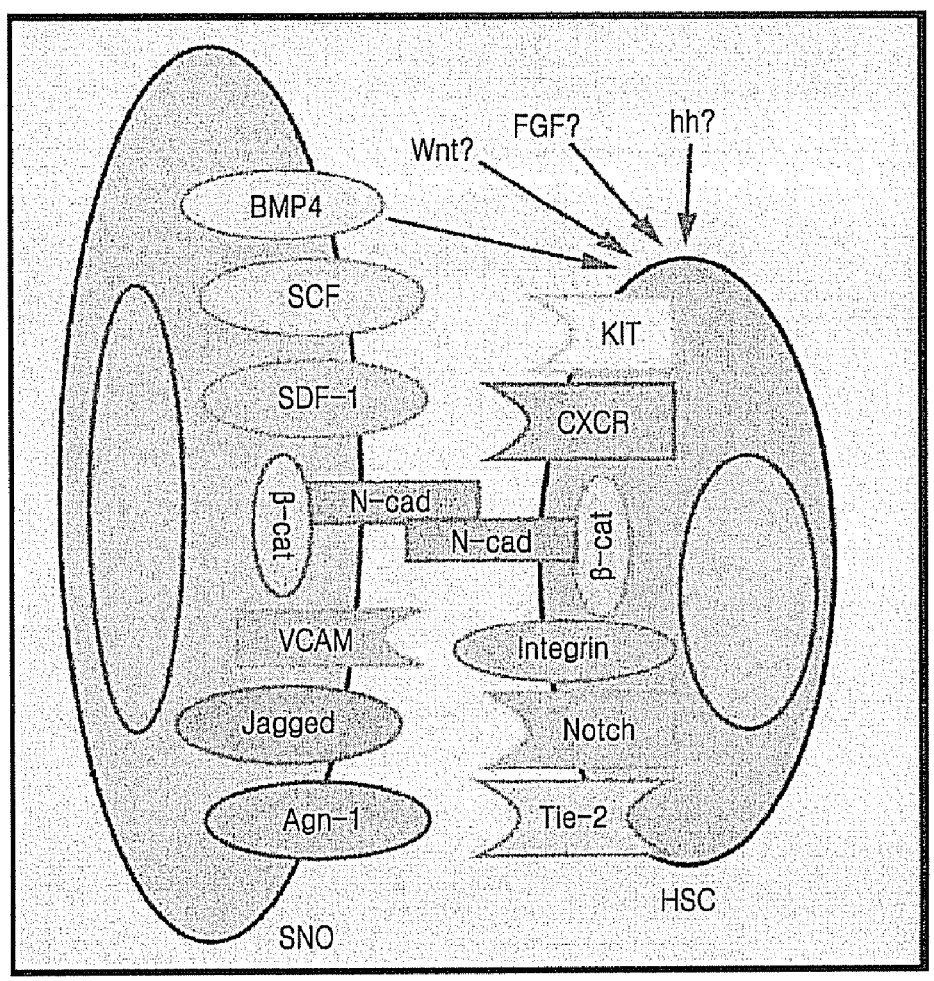
FIG. 1B is a schematic view illustrating interactions between the HSC and the SNO via N-cadherin in order for the HSC to retain stemness.
Figure 2:
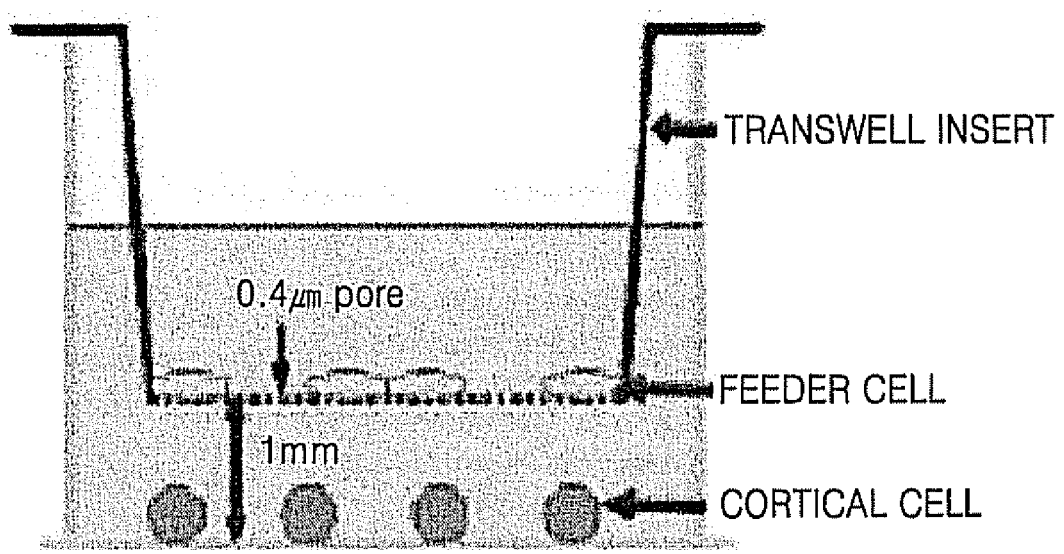
FIG. 2 is a schematic view illustrating a conventional transwell insert used in researching interactions between cells by a soluble factor through a liquid of the prior art.

The present invention is described more fully hereinafter with reference to the accompanying drawings, in which exemplary embodiments of the invention are shown.

This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "combined to" another element or layer, the element or layer can be directly combined to another element or layer or intervening elements or layers. In contrast, when an element is referred to as being "directly combined" to another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or." The terms "comprising" and "including" are to be construed as open-ended terms (i.e., meaning "including, but not limited to").

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Figure 3:
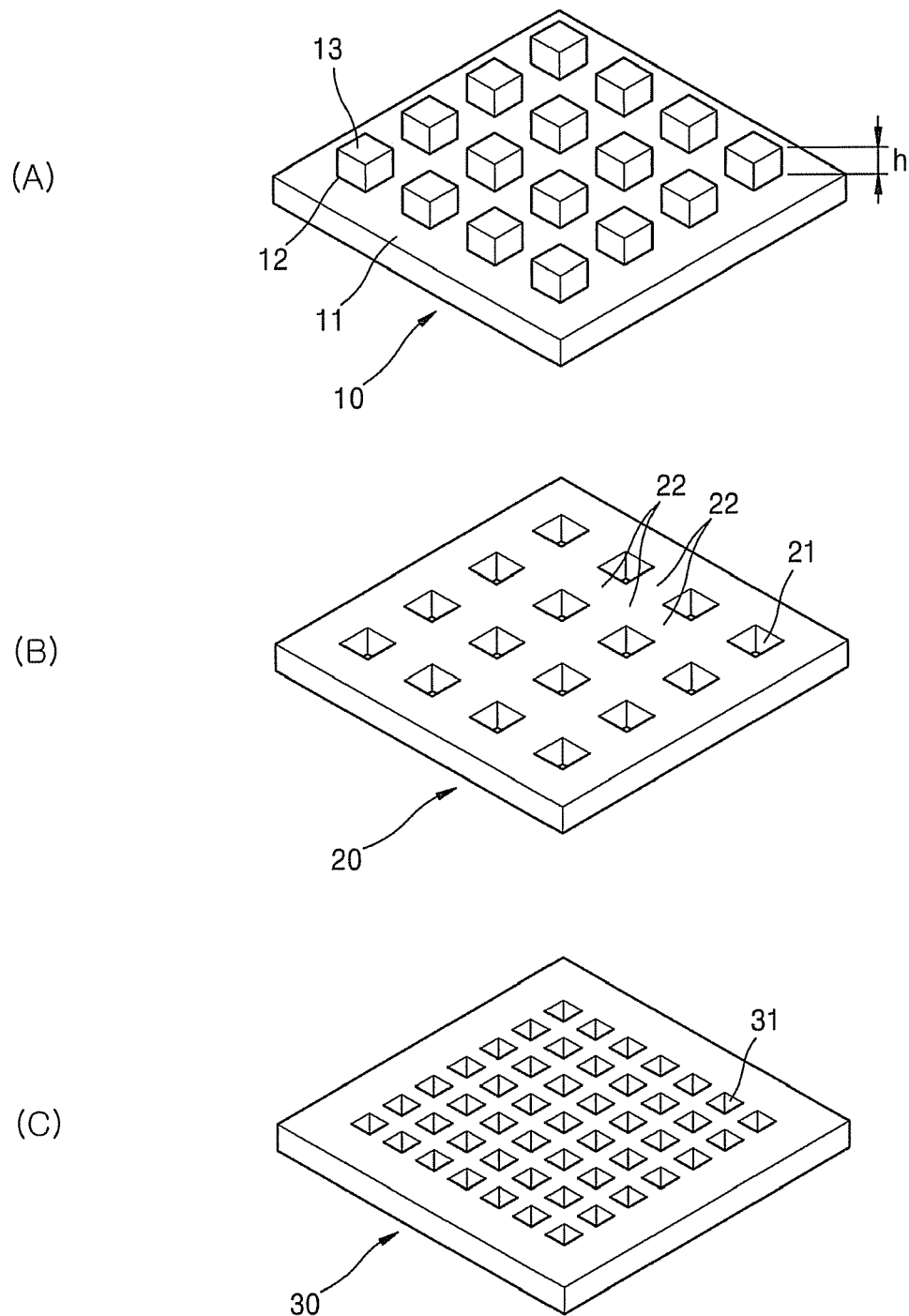
FIGS. 3A-3C are schematic perspective views illustrating exemplary embodiments of substrates of a cell co-culture apparatus for researching the interactions between cells according to the present invention.

FIGS. 3A-3C illustrate exemplary embodiments of the substrates of a cell co-culture apparatus for researching interactions between cells according to the present invention.

Figure 4A:
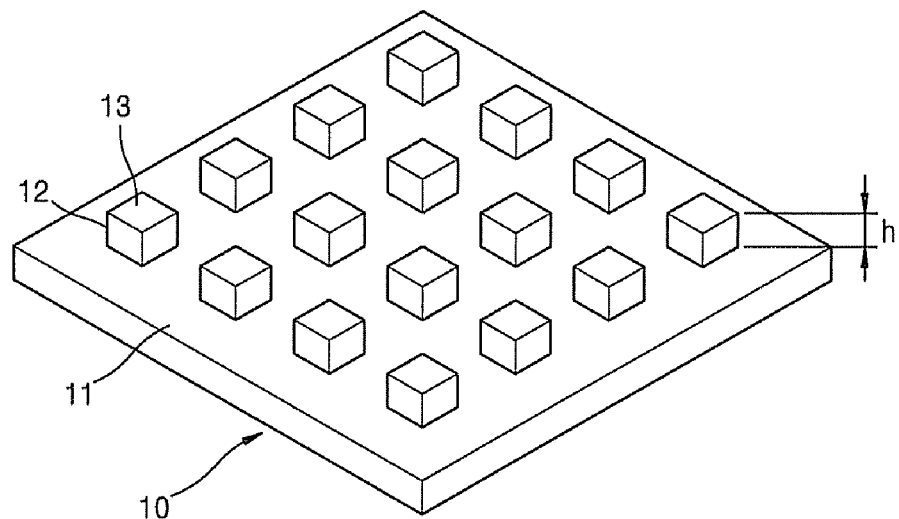
FIG. 4A is a schematic perspective view illustrating an exemplary embodiment of a first substrate of a cell co-culture apparatus for researching the interactions between cells according to the present invention.
Figure 4B:
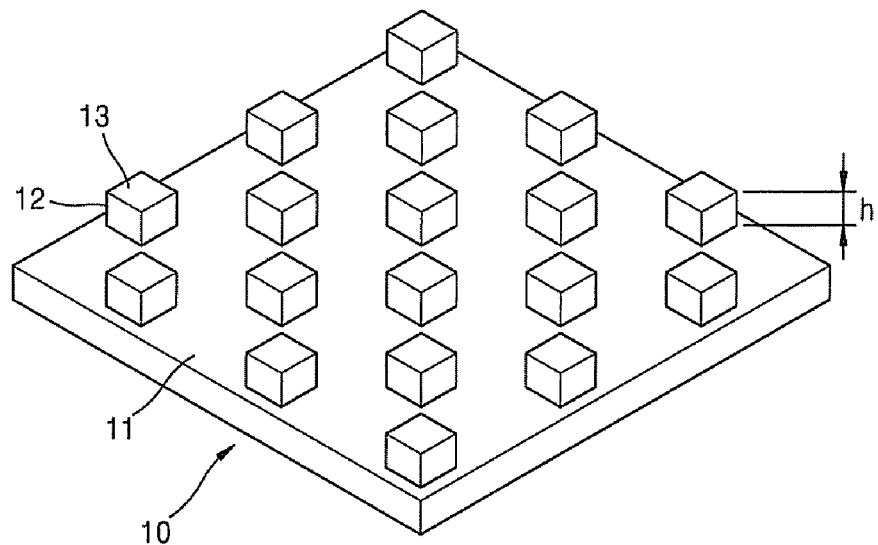
FIG. 4B is a schematic perspective view illustrating another exemplary embodiment of a first substrate of a cell co-culture apparatus for researching the interactions between cells according to the present invention.
Figure 5:
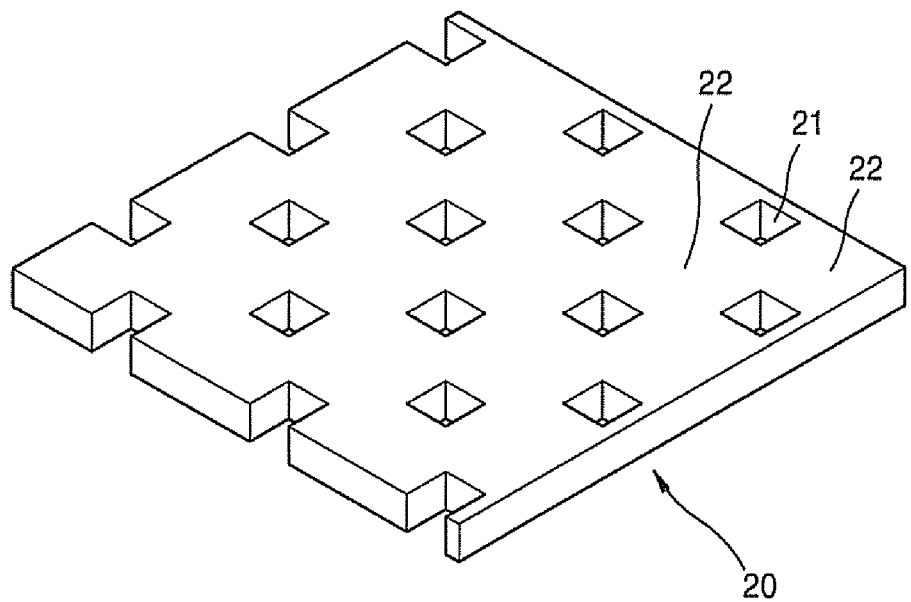
FIG. 5 is a schematic perspective view illustrating an exemplary embodiment of a second substrate of a cell co-culture apparatus for researching the interactions between cells according to the present invention.
Figure 6:
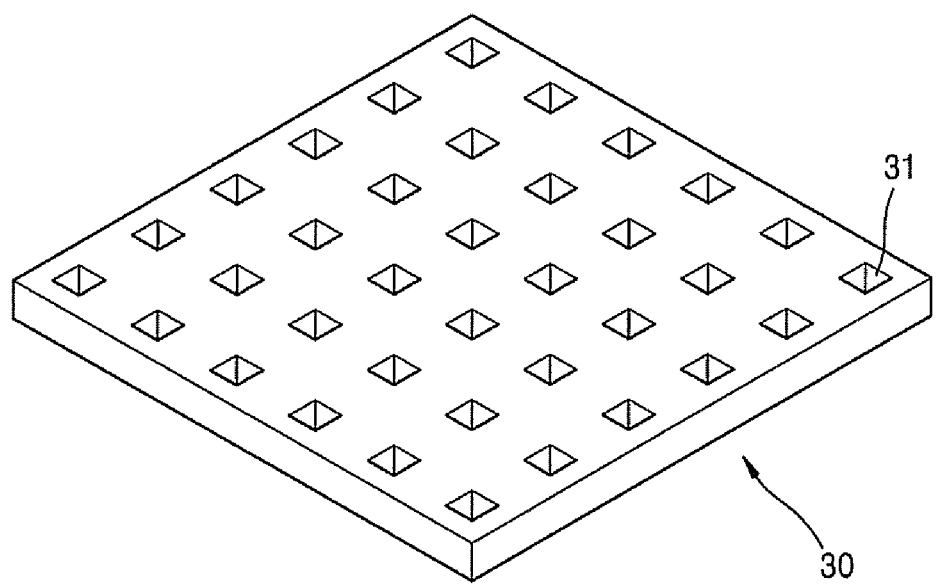
FIG. 6 is a schematic perspective view illustrating an exemplary embodiment of a third substrate of a cell co-culture apparatus for researching the interactions between cells according to the present invention.

Referring to FIGS. 3A-3C, the cell co-culture apparatus includes a first substrate 10, a second substrate 20 and a third substrate 30. Exemplary embodiments of the first substrate 10 are illustrated in FIGS. 4A and 4B. Exemplary embodiments of the second substrate 20 and the third substrate 30 are illustrated in FIGS. 5 and 6, respectively.

In the cell co-culture apparatus, the first substrate 10, the second substrate 20, and the third substrate 30 are sequentially disposed, so that cells may be seeded through channels 31 of the third substrate 30. The third substrate 30 is separated from the second substrate 20 and the cells are cultured. The illustrated embodiment of the cell co-culture apparatus includes the three substrates, for example, first substrate 10, second substrate 20, and third substrate 30, but the invention is not limited thereto.

The first substrate 10 includes a plurality of projections 12 on a surface 11 (e.g., upper surface) of the first substrate. Each of the projections 12 has a substantially flat top surface 13 for culturing cells. The flat top surfaces 13 of the projections 12 are portions of the first substrate 10 on which the cells are seeded and cultured. The projections 12 may have a sufficient quantity and/or dimension of the flat top surfaces 13 such that the cells can be seeded and cultured.

The projections 12 may have any one or a combination of various shapes. In exemplary embodiments, projections may have a shape including, but not limited to, a cylinder or a polygonal pillar, such as a cube. A height "h" of the projections 12 is not specifically limited. That is, the height of the projections 12 may be adjusted such that a difference between the height of the projections 12 (e.g., at the top surfaces 13 measured from the upper surface of the first substrate 10) and the thickness of the second substrate 20 (e.g., from the upper surface to a lower or bottom surface of the second substrate 20) allows interactions between the cells seeded on the substrate surfaces 22 provided between channels 21 of the second substrate 20 and the cells seeded on the flat top surfaces 13 of the first substrate 10 during the co-culture.

The number of the projections 12 of the first substrate 10 is not specifically limited, and may vary depending on an intended number of portions on which the cells are to be seeded during the co-culture. In exemplary embodiments, the number of projections 12 may be more or less than that shown in FIGS. 3, 4A and 4B.

The projections 12 may be arranged in any of a number of patterns. As illustrated in FIGS. 3A and 4A, the projections 12 may be arranged in a substantially matrix formation including a number of rows and columns. Alternative exemplary embodiments may have the projections 12 in a formation including the projections 12 staggered in a row and columns formation instead of aligned in rows and columns, as illustrated in FIG. 4B, but the arrangement of the projections 12 is not limited thereto.

FIG. 5 illustrates an exemplary embodiment of the second substrate 20 which is included in a cell co-culture apparatus for researching the cell interactions according to the present invention. As illustrated, the second substrate 20 illustrated in FIG. 5 may be coupled with the exemplary first substrate 10 illustrated in FIG. 4B.

The second substrate 20 is a substrate for seeding and culturing the second cells that are to be investigated for cell interactions. The second substrate 20 includes the same number of channels 21 as the number of projections 12 of the first substrate 10 illustrated in FIG. 4B. The channels 21 fit with the projections 12 of the first substrate 10 when the second substrate 20 is disposed above or over the first substrate 10.

The cells are seeded and cultured on the substrate surfaces 22 between the channels 21 of the second substrate 20. The channels 21 of the second substrate 20 may have a shape that corresponds with the projections 12 of the first substrate 10. The shapes and positions of the channels 21 of the second substrate 20 vary depending on the shapes and positions of the projections 12 of the first substrate 10.

The size (e.g., width taken parallel to the substrate surfaces 22) of the channels 21 of the second substrate 20 may be substantially the same as the size of the cross-sections of the projections 12. However, when the second substrate 20 is disposed on the first substrate 10, an interval "a" between edges of the flat top surfaces 13 of the projections 12 of the first substrate 10 and inner surfaces of the substrate surfaces 22 at the channels 21 of the second substrate 20 (see FIG. 8) may be present. Interval "a" may be considered a gap between outer surfaces of the projections 12 and the inner surfaces of the channel 21 taken in a direction parallel to the substrate surfaces 22. The interval "a" may be sufficiently narrow such that the cells on the flat top surfaces 13 of the projections 12 of the first substrate 10 can interact with the cells on the substrate surfaces 22. The interval "a" depends on the types of co-cultured cells. In one exemplary embodiment, the interval "a" may be about 10 micrometers (μm) to about 20 μm.

Furthermore, the interval "a" may be adjusted in ways to determine the effects of the distance between the cells on the interactions between the cells.

In one embodiment, the thickness of the second substrate 20 may be the same as the height "h" of the projections 12 of the first substrate 10 so as to allow the interactions between the cells cultured on the flat top surfaces 13 of the projections 12 of the first substrate 10 and the cells cultured on the substrate surfaces 22 provided between the channels 21 of the second substrate 20.

In an alternative embodiment, the thickness of the second substrate 20 may be different from the height "h" of the projections 12 of the first substrate 10 so that such a difference allows or promotes the interactions between the cells. Such difference is substantially small and depends on the types of co-cultured cells. In one exemplary embodiment, the difference may be about 10 μm to about 20 μm.

FIG. 6 illustrates an exemplary embodiment of a third substrate 30 included in a cell co-culture apparatus for researching interactions between cells according to the present invention. As illustrated, the third substrate 30 illustrated in FIG. 6 may be coupled with the first substrate 10 illustrated in FIG. 4B and the second substrate 20 illustrated in FIG. 5.

The third substrate 30 has a plurality of channels 31 through which the cells may easily be seeded on the flat top surfaces 13 of the projections 12 of the first substrate 10 and the substrate surfaces 22 between the channels 21 of the second substrate 20. The third substrate 30 includes a plurality of channels 31 that may correspond in number, arrangement and/or dimension with the flat top surfaces 13 of the projections 12 of the first substrate 10. The plurality of channels 31 may also correspond with the substrate surfaces 22 between the channels 21 of the second substrate 20.

An arrangement of the channels 31 of the third substrate 30 may vary depending on the positions of the projections 12 of the first substrate 10 and the substrate surfaces 22 between the channels 21 of the second substrate 20. In exemplary embodiments if a cross-section of the channels 31 of the third substrate 30 is rectangular the cross-section of the channels 31 may be in any of a number of shapes that allow the introduction of the cells into the channels 31, such as a circle or a polygon.

A thickness of the third substrate 30 may be any of a number of thicknesses that allow a relatively easy introduction of the cells. The thickness of the third substrate may be about 50 μm to about 100 μm.

In an exemplary embodiment cell co-culture apparatus according to the present invention, the width (e.g., taken in a direction parallel to the surface 11), length (e.g., taken in a direction parallel to the surface 11), and height (e.g., taken in a direction perpendicular to the surface 11) of the projections 12 of the first substrate 10 may each be about 50 μm-to about 100 μm.

A width and length (e.g., taken in a direction parallel to the surfaces 22) of the channels 21 of the second substrate 20 and the thickness (e.g., taken in a direction perpendicular to the surfaces 22) of the second substrate 20 may each be about 50 μm to about 140 μm.

A width and length (e.g., taken in a direction parallel to the surfaces 22) of the channels 31 of the third substrate 30 and the thickness (e.g., taken in a direction perpendicular to the surfaces 22) of the third substrate 30 may each be about 50 μm to about 100 μm. However, the dimensions of the projections 12, channels 21 and channels 31 described above are not limited thereto.

In one exemplary embodiment, the width, length and height of the projections 12 of the first substrate 10 may be about 0.1 millimeter (mm)×0.1 millimeter (mm)×0.1 millimeter (mm), respectively. The width and length of the channels 21 of the second substrate 20 may be about 0.14 mm×0.14 mm, respectively, and the thickness of the second substrate 20 may be about 0.1 mm. The width and length of the channels 31 of the third substrate 30 may be about 0.09 mm×0.09 mm, respectively, and the thickness of the third substrate 30 may be about 0.1 mm.

FIGS. 7A-7C are schematic perspective views illustrating an exemplary embodiment of a method of sequentially disposing a second substrate 20 and a third substrate 30 on a first substrate 10 of a cell co-culture apparatus according to the present invention.

The first substrate 10 further includes a plurality of fixing pillars 14 and the second substrate 20 and the third substrate 30 further include a plurality of fixing channels 23 and 33 into which the fixing pillars 14 are inserted. In the cell co-culture apparatus, the first substrate 10 further includes the plurality of fixing pillars 14 on the first substrate surface 11 such that the second substrate 20 and the third substrate 30 can be stably disposed on the first substrate 10. The second substrate 20 and the third substrate 30 further include the fixing channels 23 and 33 into which the fixing pillars 14 provided on a first substrate surface 11 are inserted.

Since the fixing pillars 14 on the first substrate 10 are intended to stably fix the first substrate 10 with the second substrate 20 and the third substrate 30, the number of the fixing pillars 14 is not specifically limited and the fixing pillars 14 may be present in any of a number positions as long as the positions of the fixing pillars 14 do not affect the interactions between the cells.

The fixing pillars 14 may be in any of a number of pillar shapes including, but not limited to, a cylinder and a polygonal pillar, provided that the fixing channels 23 and 33 correspond to the shape and/or dimensions of the fixing pillars 14 and fit with the corresponding fixing pillars 14.

Figure 7:
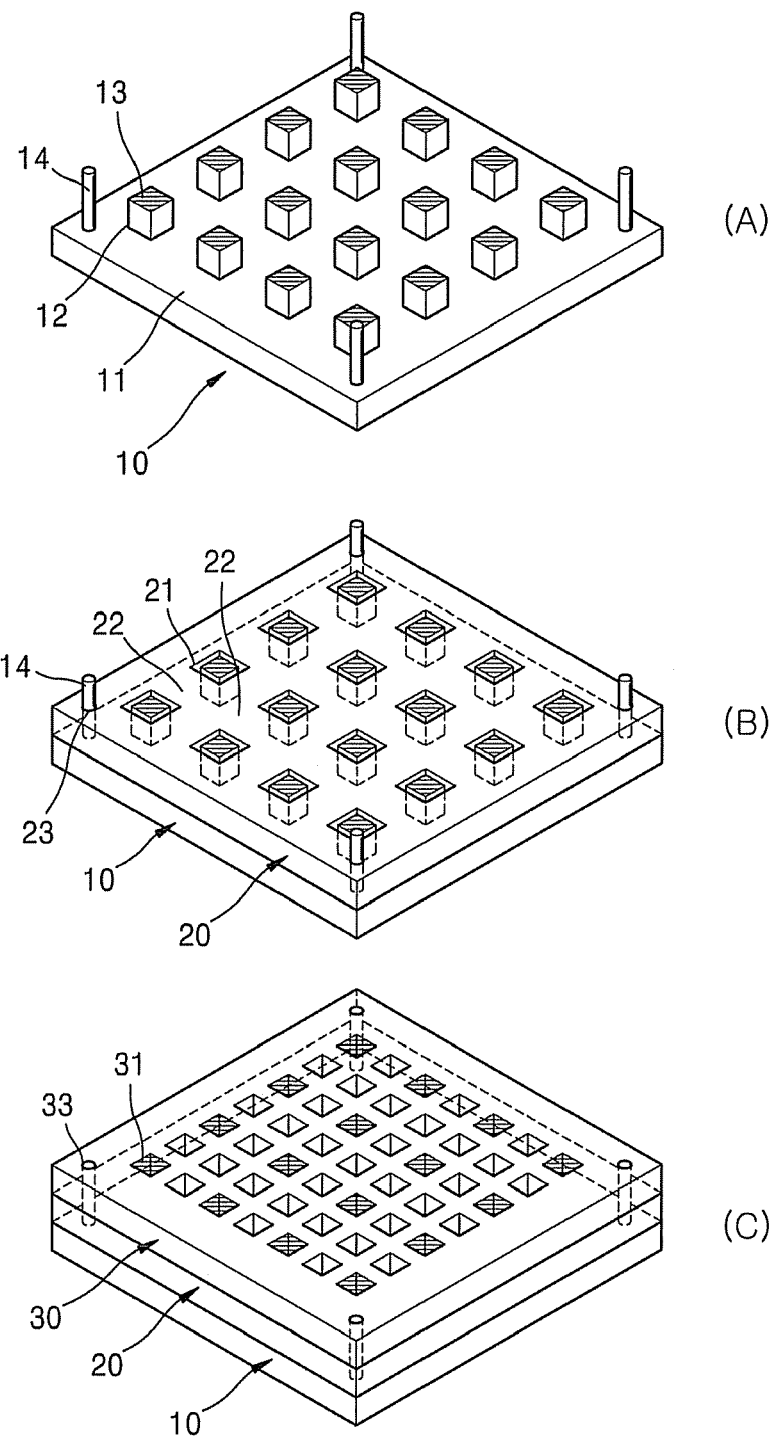
FIG. 7 is a schematic perspective view illustrating an exemplary embodiment of a method of sequentially disposing a second substrate and a third substrate on a first substrate of a cell co-culture apparatus according to the present invention, in which the first substrate further includes a plurality of fixing pillars and the second substrate and the third substrate further includes a plurality of fixing channels into which the fixing pillars are inserted.

Referring to FIG. 7, the first substrate 10 has one fixing pillar 14 in the shape of a cylinder in each of the corners of the first substrate 10 The second substrate 20 and the third substrate 30 have the fixing channels 23 and 33 in corresponding corners such that the fixing channels 23 and 33 can correspondingly fit with the fixing pillars 14.

Referring to FIGS. 7A and 7B, the second substrate 20 is combined with the first substrate 10, such as be adhering the substrates to each other. The pillars 14 are inserted into the fixing channels 23. The projections 12 are inserted into corresponding channels 21.

Referring to FIG. 7C, the third substrate 30 is disposed on the upper surface of the second substrate 20 and combined with the second substrate 20, such as by adhering. A portion of the pillars 14 protruding from surfaces 22 are inserted into the fixing channels 33. As illustrated, the third substrate 30 has a larger number of channels 31 than projections 12 of the first substrate and channels 21 of the second substrate, but the invention is not limited thereto. A portion of the channels 31 correspond in location to the projections 12 and the channels 21. A remaining portion of the channels 31 are interposed between positions of the projections 12 and the channels 21 and face the surfaces 22 of the second substrate 20.

In exemplary embodiments, the three substrates may be disposed on each other in a sequence or may be disposed at a substantially same time.

The cell co-culture apparatus may be used to determine the interactions between different types of cells by co-culturing the cells and separating one type of cells from another type of cells. FIG. 10 illustrates an exemplary method of co-culturing and isolating cells using an exemplary embodiment of a laminated form of a cell co-culture apparatus, illustrated in FIGS. 8 and 9, according to the present invention.

Figure 8:
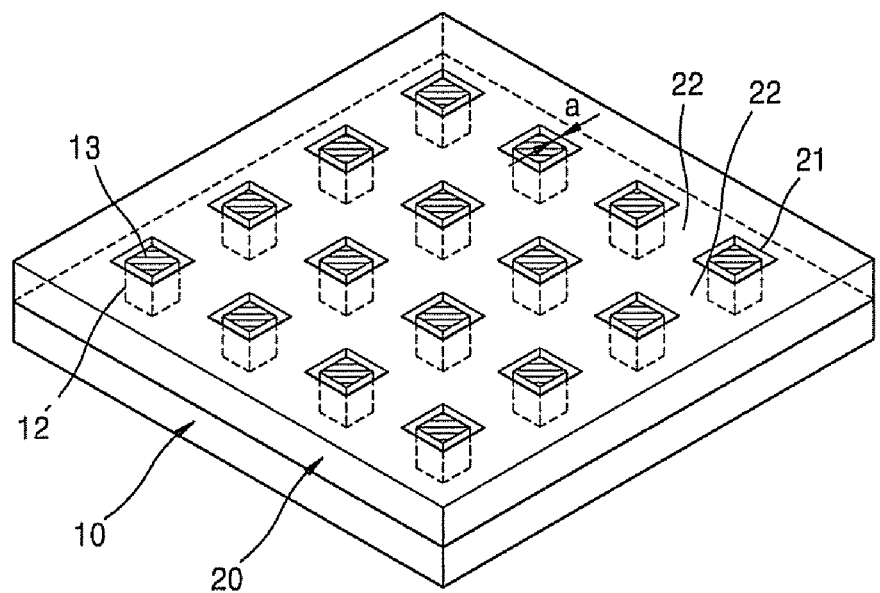
FIG. 8 is a schematic perspective view illustrating an exemplary embodiment of a laminated form of the cell co-culture apparatus according to the present invention in which the second substrate is disposed on the first substrate.

To research the interactions between the cells using the cell co-culture apparatus, referring to FIG. 8, the second substrate 20 is disposed on the first substrate 10. The second substrate 20 is disposed on the first substrate 10 such that the channels 21 of the second substrate 20 fit with the projections 12 of the first substrate 10. As in the illustrated embodiment, there may be a difference between the height "h" of the projections 12 of the first substrate 10 and the thickness of the second substrate 20. In an alternative embodiment, the height "h" of the projections 12 of the first substrate 10 may be substantially the same as the thickness of the second substrate 20 such that the flat top surfaces 13 of the projections 12 of the first substrate 10 and the substrate surfaces 22 of the second substrate 20 form a substantially flat surface after lamination.

Figure 9:
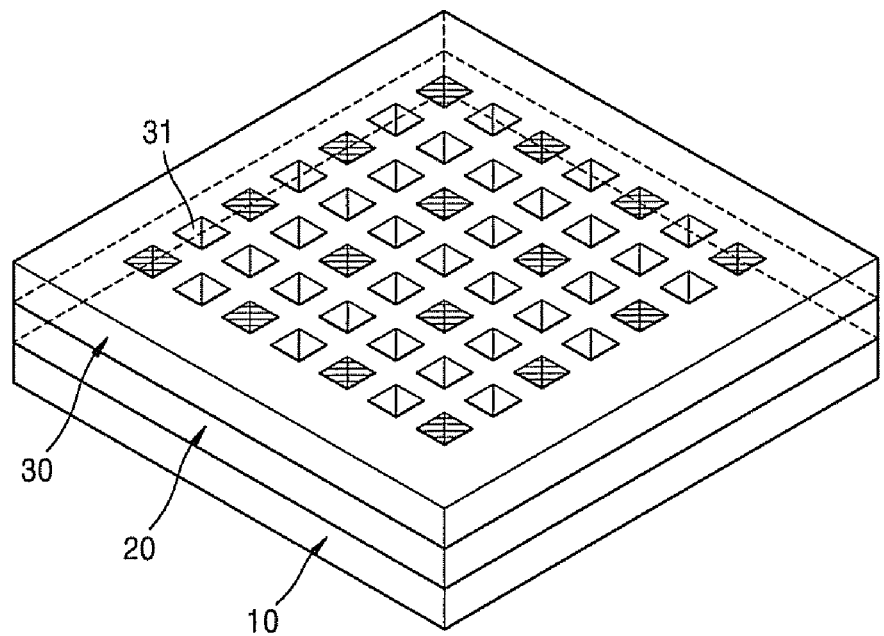
FIG. 9 is a schematic perspective view illustrating another exemplary embodiment of a laminated form of the cell co-culture apparatus according to the present invention in which the second substrate is disposed on the first substrate and the third substrate is disposed on the second substrate.
Figure 10:
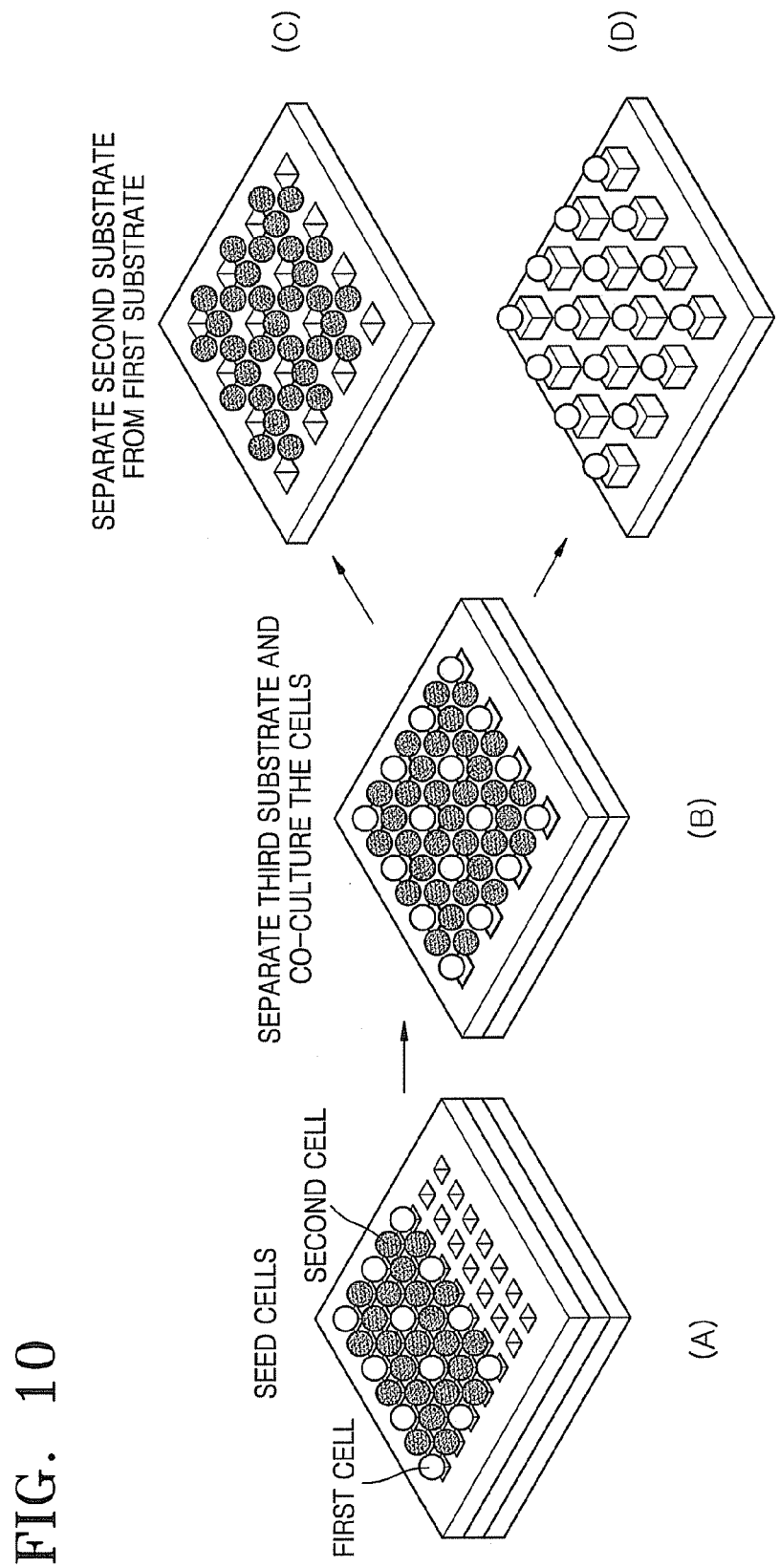
FIG. 10 illustrates an exemplary embodiment of a method of co-culturing and isolating cells according to the present invention using the cell co-culture apparatus.

Referring to FIG. 9, the third substrate 30 is disposed on the second substrate 20 such that a plurality of channels 31 of the third substrate 30 corresponds with the flat top surfaces 13 of the projections 12 of the first substrate 10 and the substrate surfaces 22 between the channels 21 of the second substrate 20, respectively. FIG. 9 is a schematic perspective view illustrating an exemplary embodiment of a laminated form of the cell co-culture apparatus formed by disposing the first substrate 10, the second substrate 20, and the third substrate 30 sequentially, according to the present invention.

Referring to FIG. 10A, after the third substrate 30 is disposed on the second substrate 20, first cells (e.g., the white cells) are seeded on the flat top surfaces 13 of the projections 12 of the first substrate 10 and second cells (e.g., the shaded cells), different from the first cells, are seeded on the substrate surfaces 22 between the channels 21 of the second substrate 20 through open channels 31 of the third substrate 30 facing the substrate surfaces 22. Since the first cells are different from the second cells, since the first cells and the second cells may be cultured on the flat top surfaces 13 of the projections 12 of the first substrate 10 and the substrate surfaces 22 between the channels 21 of the second substrate 20, respectively, the interactions between the cells by direct contact may occur.

In one embodiment, all the first cells that are seeded on the flat top surfaces 13 of the projections 12 of the first substrate 10 may be identical. In an alternative embodiment, to simultaneously research the interactions between various combinations of cells, the first cells may include different types of cells seeded on the flat top surfaces 13 of the projections 12 of the first substrate 10 through each of the channels 31 of the third substrate 30.

In one embodiment, all the second cells that are seeded on the substrate surfaces 22 between the channels 21 of the second substrate 20 may be identical. In an alternative embodiment, to simultaneously research the interactions between various combinations of cells, the second cells may include different types of cells seeded on the substrate surfaces 22 between the channels 21 of the second substrate 20 through each of the channels 31 of the third substrate 30.

Once a desired combination of first and second cells are seeded on the flat top surfaces 13 of the projections 12 of the first substrate 10 and the substrate surfaces 22, respectively, through the channels 31 of the third substrate 30, the third substrate 30 is separated from the second substrate 20 and the first and second cells are co-cultured. (FIG. 10B) The cell co-culture allows direct contact between the first cells on the flat top surfaces 13 and the second cells on the substrate surfaces 22 to occur after the separation of the third substrate 30.

When the cell co-culture is completed, the second substrate 20 is separated from the first substrate 10. (FIGS. 10C and 10D.) The resulting cells are taken and observed in order to determine whether changes occurred in each of the first cells and the second cells. Due to the easy separation of the first substrate 10 from the second substrate 20, changes occurring in each of the first cells and the second cells due to the direct contact between the different cells may be determined.

Figure 11:
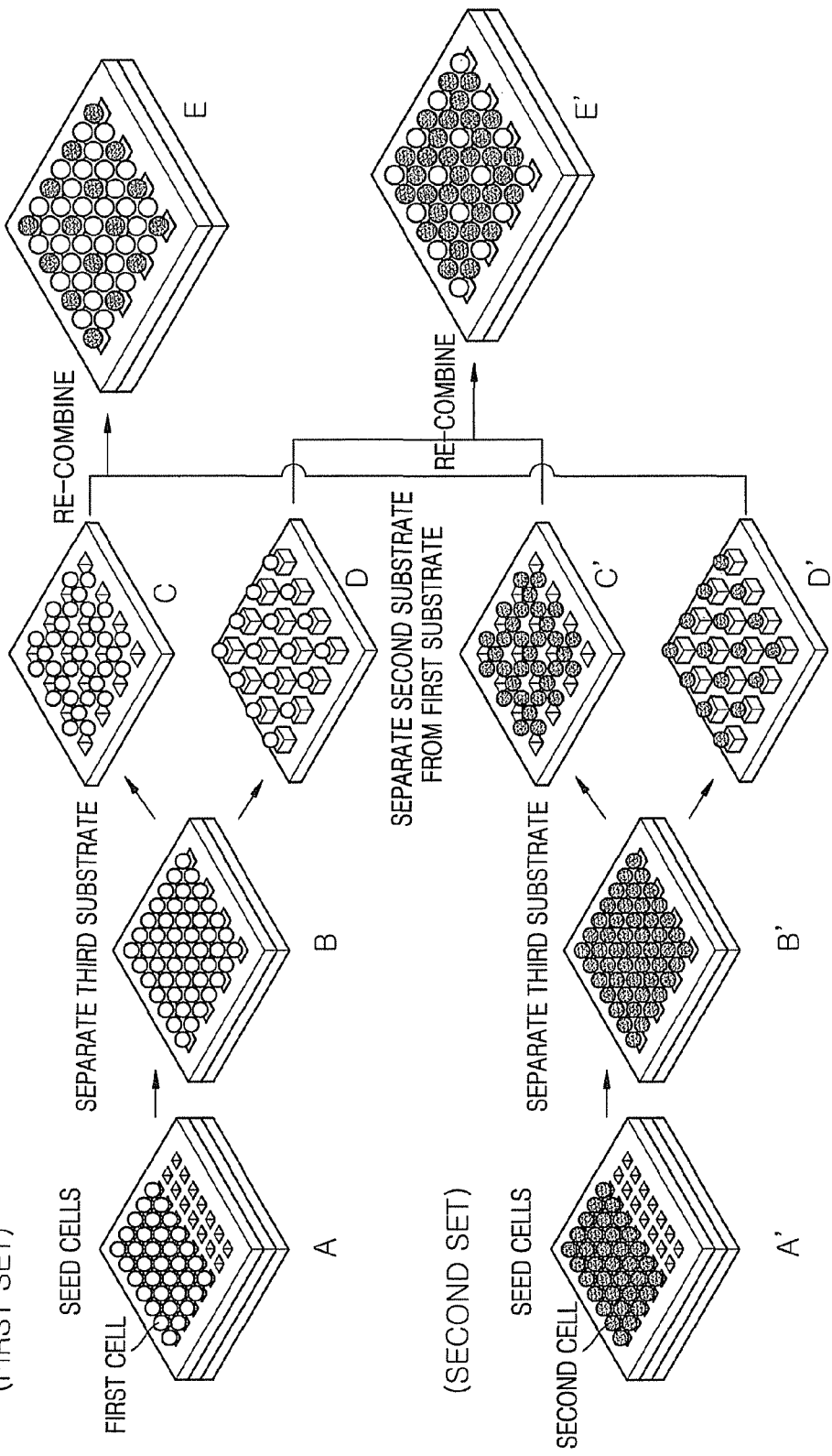
FIG. 11 illustrates another exemplary embodiment of a method of co-culturing and isolating cells according to the present invention using the cell co-culture apparatus.

The cell co-culture apparatus may be used in different ways. FIG. 11 illustrates another exemplary embodiment of a method of using the cell co-culture apparatus according to the present invention.

Two cell co-culture apparatuses of the illustrated embodiments are prepared. In each set of the substrates of the cell co-culture apparatuses, a second substrate 20 is disposed on a first substrate 10 such that a plurality of channels 21 of the second substrate 20 fit with a plurality of projections 12 of the first substrate 10. Then, a third substrate 30 is disposed on the second substrate 20 such that a plurality of channels 31 of the third substrate 30 correspond with the flat top surfaces 13 of the projections 12 of the first substrate 10 and substrate surfaces 22 between the channels 21 of the second substrate 20.

The first cells are seeded through all the channels 31 of the third substrate 30 in the first cell co-culture apparatus (FIG. 11A), and the second cells are seeded through all the channels 31 of the third substrate 30 in the second cell co-culture apparatus (FIG. 11A'). The first substrate 10, the second substrate 20, and the third substrate 30 in each of the first and second cell co-culture apparatuses are separated from each other (FIGS. 11B, 11B', 11C, 11C', 11D and 11D').

As illustrated in FIGS. 11E and 11E', the first substrate 10 and second substrate 20 of the first cell co-culture apparatus (e.g., first set) and the first substrate 10 and second substrate 20 of the second cell co-culture apparatus (e.g., second set) are alternately disposed. That is, the second substrate 20 of the second cell co-culture apparatus is disposed on the first substrate 10 of the first cell co-culture apparatus and the second substrate 20 of the first cell co-culture apparatus is disposed on the first substrate 10 of the second cell co-culture apparatus such that the channels 21 of the second substrate 20 fit with the projections 12 of the first substrate 10.

Cell culture is performed on each set of substrates illustrated in FIGS. 11A to 11E'. When the cell culture is completed, each of the second substrates 20 is separated from their respective first substrate 10 and the results of the changes that occurred in each of the cells may be determined.

Hereinafter, the present invention will be described in more detail with reference to the following examples. However, these examples are provided for the purpose of illustration and are not intended to limit the scope of the invention.

Example 1

Co-Culture of Cells

A cell co-culture apparatus was prepared using a first substrate 10, a second substrate 20, and a third substrate 30 as illustrated in FIGS. 4B, 5 and 6, respectively. A substrate portion of the first substrate 10, but not the projections 12 of the first substrate 10, was formed of glass, and the projections 12 of the first substrate 10, the second substrate 20, and the third substrate 30 were formed of SU-8 (Microchem).

The width, length, and height of the projections 12 of the first substrate 10 were 50 μm. The width and length of the channels 21 of the second substrate 20 and the thickness of the second substrate 20 were 50 μm. The width and length of the channels 31 of the third substrate 30 and the thickness of the third substrate 30 were 50 μm.

The first substrate 10, the second substrate 20, and the third substrate 30 were sequentially disposed. Then, A549 cells, which are human cells, were inoculated on the apparatus through the channels 31 of the third substrate 30. For each of the channels 31 of the third substrate 30, two to five cells were inoculated. Subsequently, the third substrate 30 was separated from the second substrate 20, and then the flat top surfaces 13 of the first substrate 10 and the substrate surfaces 22 of the second substrate 20 on which the cells were inoculated were photographed using a phase-contrast microscope. The photographs are indicated as A and C in FIG. 12.

To confirm whether the cells observed on the above substrates are alive, the cells were fluorescence-stained with CellTracker™ Green CMFDA (5-Chloromethylfluorescein Diacetate) or CellTracker™ Red (Invitrogen), and photographed using a fluorescence microscope. The photographs are indicated as B and D in FIG. 12. FIG. 12B illustrates the cells stained with CellTracker™ Green CMFDA (Invitrogen) emitting green fluorescence (color not shown) and FIG. 12D shows the cells stained with CellTracker™ Red CMTPX (Invitrogen) emitting red fluorescence (color not shown).

A through D of FIG. 12 show that the cells are uniformly distributed on the top surfaces of the projections 12 of the first substrate 10 and on the substrate surfaces 22 between the channels 21 of the second substrate 20.

Example 2

Isolation of Co-Cultured Cells

The cells that were inoculated in Example 1 were cultured at 37° C. for 24 hours after the separation of the third substrate 30 from the second substrate 20. Then, the first substrate 10 and the second substrate 20 were separated from each other. The cells on the first substrate 10 and the cells on the second substrate 20 were fluorescence-stained with CellTracker™ Green CMFDA (Invitrogen) or CellTracker™ Red CMTPX (Invitrogen), and photographed using a fluorescence microscope. The photographs are illustrated in FIG. 13.

A and B in FIG. 13 illustrate the cells stained with CellTracker™ Green CMFDA (Invitrogen) emitting green fluorescence (color not shown). C and D in FIG. 13 illustrate the cells stained with CellTracker™ Red CMTPX (Invitrogen) emitting red fluorescence (color not shown).

A and C in FIG. 13 represent the cells cultured on the substrate surfaces 22 between the channels 21 of the second substrate 20. B and D in FIG. 13 represent the cells cultured on the flat top surfaces 13 of the projections 12 of the first substrate 10. It can be confirmed from A and C that the cells cultured on the projections 12 of the first substrate 10 (shown in B and D) were separated from the cells on the substrate surfaces 22 of the second substrate 20. In B and D in FIG. 13, the cells cultured on portions other than the projections 12 of the first substrate 10, such as the cells cultured on the portions of the second substrate 20 (shown in A and C), were removed.

It can be confirmed from the above results that the illustrated embodiments of the co-culture apparatus allow a desired pattern of cell culture. The cells co-cultured on a combination of the first substrate 10 and the second substrate 20 can be isolated in a desired pattern by separating the first substrate 10 and the second substrate 20 from each other.

As in the illustrated embodiments, a cell co-culture apparatus for researching the interaction between the cells by direct contact is provided. Further, a method of co-culturing and isolating cells for researching the interactions between the cells by direct contact between the cells is provided using the cell co-culture apparatus.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cell co-culture apparatus comprising:
   a first substrate comprising:
      a substrate portion; and
      a plurality of projections on a surface of the substrate portion, wherein the projections include top surfaces for culturing cells;
   a second substrate comprising:
      a same number of first channels as a number of the projections of the first substrate such that the first channels fit with the projections of the first substrate; and
      cell culturing substrate surfaces interposed between the first channels; and a third substrate comprising:
      a plurality of second channels corresponding with the top surfaces of the projections of the first substrate, and
      a plurality of third channels corresponding with the cell culturing substrate surfaces of the second substrate.

2. The cell co-culture apparatus of claim 1, wherein the first substrate further comprises at least one fixing pillar and the second substrate and the third substrate each further comprise at least one fixing channel into which the at least one fixing pillar is inserted.

3. The cell co-culture apparatus of claim 1, wherein a thickness of the second substrate is the same as a height of the projections of the first substrate.

4. The cell co-culture apparatus of claim 1, wherein the substrate portion of the first substrate includes glass, silicon, plastics, or a combination thereof.

5. The cell co-culture apparatus of claim 1, wherein the projections of the first substrate, the second substrate and the third substrate are each formed of a biocompatible material.

6. The cell co-culture apparatus of claim 5, wherein the biocompatible material is SU-8.

7. The cell co-culture apparatus of claim 1, wherein a width, a length, and a height of the projections of the first substrate are each about 50 μm to about 100 μm.

8. The cell co-culture apparatus of claim 7, wherein a width and a length of the first channels of the second substrate and a thickness of the second substrate are each about 50 μm to about 100 μm.

9. The cell co-culture apparatus of claim 8, wherein a width and a length of each of the second and the third channels of the third substrate and a thickness of the third substrate are each about 50 μm to about 100 μm.

10. The cell co-culture apparatus of claim 1, wherein a total number of the second channels and the third channels is greater than the number of first channels.

11. A method of co-culturing and isolating cells using a cell co-culture apparatus, the method comprising:
- disposing a second substrate on a first substrate such that a plurality of first channels of the second substrate fit with a plurality of projections of the first substrate;
- disposing a third substrate on the second substrate such that a plurality of second channels of the third substrate correspond with top surfaces of the plurality of projections of the first substrate and cell culturing substrate surfaces between the first channels of the second substrate;
- seeding first cells on the top surfaces of the projections of the first substrate through the second channels of the third substrate;
- seeding second cells on the cell culturing substrate surfaces between the first channels of the second substrate through the second channels of the third substrate;
- separating the third substrate from the second substrate and culturing the cells; and
- separating the second substrate from the first substrate;

wherein the co-culture apparatus comprises:
- the first substrate comprising:
  - a substrate portion; and
  - the plurality of projections on a surface of the substrate portion, wherein the projections include the top surfaces for culturing cells;
- the second substrate comprising:
  - a same number of the first channels as a number of the projections of the first substrate such that the first channels fit with the projections of the first substrate; and
  - cell culturing substrate surfaces interposed between the first channels; and the third substrate comprising:
    - a portion of the plurality of second channels corresponding with the top surfaces of the projections of the first substrate, and a remaining portion of the plurality of second channels corresponding with the cell culturing substrate surfaces of the second substrate.

12. The method of claim 11, wherein a same type of the first cells are seeded on each of the top surfaces of the projections of the first substrate.

13. The method of claim 11, wherein different types of the first cells are seeded on each of the top surfaces of the projections of the first substrate.

14. The method of claim 11, wherein a same type of the second cells are seeded on each of the cell culturing substrate surfaces between the first channels of the second substrate.

15. The method of claim 11, wherein different types of the second cells are seeded on each of the cell culturing substrate surfaces between the first channels of the second substrate.

16. The method of claim 11, wherein the disposing a second substrate on a first substrate includes inserting at least one fixing pillar disposed on the first substrate into a first fixing channel of the second substrate.

17. The method of claim 16, wherein the disposing a third substrate on the second substrate includes inserting the at least one fixing pillar into a second fixing channel of the third substrate.

18. A method of co-culturing and isolating cells using a cell co-culture apparatus, the method comprising:
- disposing a second substrate on a first substrate such that a plurality of first channels of the second substrate fit with a plurality of projections of the first substrate, for each of a first set of the substrates and a second set of the substrates, respectively, a first co-culture apparatus including the first set of the substrates and a second co-culture apparatus including the second set of the substrates;
- disposing a third substrate on the second substrate such that a plurality of second channels of the third substrate correspond with top surfaces of the projections of the first substrate and cell culturing substrate surfaces between the first channels of the second substrate, respectively, for each of the first set of the substrates and the second set of the substrates,
- seeding first cells through all of the second channels of the third substrate in the first cell co-culture apparatus, seeding second cells through all of the second channels of the third substrate in the second cell co-culture apparatus, and separating the first substrate, the second substrate, and the third substrate from each other, respectively, for each of the first and second cell co-culture apparatuses
- disposing the second substrate of the second cell co-culture apparatus on the first substrate of the first cell co-culture apparatus and disposing the second substrate of the first cell co-culture apparatus on the first substrate of the second cell co-culture apparatus such that the first channels of the second substrates of each of the first and second cell co-culture apparatus fit with the projections of each of the first substrate, respectively, and culturing the first and the second cells; and
- separating the second substrates of each of the first and second cell co-culture apparatus, respectively, from the first substrates of each of the first and second cell co-culture apparatus, respectively;

wherein the each of the first and second cell co-culture apparatus comprise:
- the first substrate comprising:
  - a substrate portion; and
  - the plurality of projections on a surface of the substrate portion, wherein the projections include the top surfaces for culturing cells;
- the second substrate comprising:
  - a same number of the first channels as a number of the projections of the first substrate such that the first channels fit with the projections of the first substrate; and
  - cell culturing substrate surfaces interposed between the first channels; and the third substrate comprising:
    - a portion of the plurality of second channels corresponding with the top surfaces of the projections of the first substrate and a remaining portion of the plurality of second channels corresponding with the cell culturing substrate surfaces of the second substrate.

* * * * *